(12) United States Patent
Schultz et al.

(10) Patent No.: US 7,687,048 B1
(45) Date of Patent: *Mar. 30, 2010

(54) AMINE TREATMENT IN LIGHT OLEFIN PROCESSING

(75) Inventors: Michael A. Schultz, Chicago, IL (US); Gavin P. Towler, Inverness, IL (US); John P. Brady, Algonquin, IL (US); William J. Lechnick, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/540,088

(22) Filed: Sep. 28, 2006

(51) Int. Cl.
*B01D 53/14* (2006.01)
*C07C 7/00* (2006.01)
*C07C 7/11* (2006.01)

(52) U.S. Cl. ............ 423/228; 95/169; 95/236; 423/220; 423/226; 585/802; 585/860

(58) Field of Classification Search .......... 423/220, 423/226, 228; 585/800, 802, 809, 860; 95/149, 95/230, 235, 236, 159–171, 239, 240
See application file for complete search history.

(56) References Cited

U.S. PATENT DOCUMENTS

| | | | |
|---|---|---|---|
| 2,813,920 A | 11/1957 | Cobb, Jr. | |
| 2,863,527 A | 12/1958 | Herbert et al. | |
| 3,409,693 A | 11/1968 | McHarg | |
| 3,552,924 A | 1/1971 | Hepp | |
| 3,702,886 A | 11/1972 | Argauer et al. | |
| 3,829,521 A | 8/1974 | Green | |
| 4,003,822 A | 1/1977 | Jo | |
| 4,072,604 A | 2/1978 | Ward | |
| 4,894,141 A | 1/1990 | Busch et al. | |
| 5,110,446 A | 5/1992 | Harandi et al. | |
| 5,360,533 A | 11/1994 | Tagamolila et al. | |
| 5,447,621 A | 9/1995 | Hunter | |
| 5,584,985 A | 12/1996 | Lomas | |
| 5,858,206 A | 1/1999 | Castillo | |
| 5,859,304 A | 1/1999 | Barchas et al. | |
| 6,110,356 A | 8/2000 | Hedrick et al. | |
| 6,139,605 A * | 10/2000 | Carnell et al. | ............. 95/164 |
| 6,464,858 B1 | 10/2002 | Brown et al. | |
| 6,538,169 B1 | 3/2003 | Pittman et al. | |
| 6,540,907 B1 | 4/2003 | Towler et al. | |

(Continued)

FOREIGN PATENT DOCUMENTS

EP 1 637 577 A2 3/2006

OTHER PUBLICATIONS

U.S. Appl. No. 11/540,110, filed Sep. 28, 2006, Schultz.

(Continued)

*Primary Examiner*—Scott Kastler
*Assistant Examiner*—Brian Walck
(74) *Attorney, Agent, or Firm*—James C. Paschall (57) ABSTRACT

Processing schemes and arrangements for the amine treatment of high olefin content (e.g., ethylene-rich) carbon dioxide-containing streams such as for the effective separation and removal of carbon dioxide therefrom are provided. Corresponding or associated processing schemes and arrangements for the catalytic cracking of a heavy hydrocarbon feedstock and obtaining light olefins substantially free of carbon dioxide via absorption-based product recovery are also provided.

19 Claims, 2 Drawing Sheets

U.S. PATENT DOCUMENTS

| | | |
|---|---|---|
| 6,576,805 B2 | 6/2003 | Keady et al. |
| 6,726,835 B2 | 4/2004 | Towler et al. |
| 6,838,587 B2 * | 1/2005 | Lattner et al. ............... 585/807 |
| 6,843,906 B1 | 1/2005 | Eng |
| 6,927,314 B1 | 8/2005 | Schultz et al. |
| 6,946,068 B2 | 9/2005 | Groten |
| 2003/0121825 A1 | 7/2003 | Pittman et al. |
| 2004/0176646 A1 * | 9/2004 | Van Egmond et al. ....... 568/699 |

OTHER PUBLICATIONS

U.S. Appl. No. 11/540,793, filed Sep. 28, 2006, Schultz.
U.S. Appl. No. 11/541,218, filed Sep. 28, 2006, Wegerer.
U.S. Appl. No. 11/541,310, filed Sep. 28, 2006, Towler.
U.S. Appl. No. 11/541,200, filed Sep. 28, 2006, Schultz.

* cited by examiner

AMINE TREATMENT IN LIGHT OLEFIN PROCESSING

BACKGROUND OF THE INVENTION

This invention relates generally to hydrocarbon processing and, more particularly, to the processing of hydrocarbon-containing materials having a high light olefin content, such as produced or formed in or by the cracking of a heavy hydrocarbon feedstock.

Light olefins serve as feed materials for the production of numerous chemicals. Light olefins have traditionally been produced through the processes of steam or catalytic cracking of hydrocarbons such as derived from petroleum sources. Fluidized catalytic cracking (FCC) of heavy hydrocarbon streams is commonly carried out by contacting a starting material whether it be vacuum gas oil, reduced crude, or another source of relatively high boiling hydrocarbons with a catalyst such as composed of finely divided or particulate solid material. The catalyst is transported in a fluid-like manner by transmitting a gas or vapor through the catalyst at sufficient velocity to produce a desired regime of fluid transport. Contact of the oil with the fluidized material catalyzes the cracking reaction.

The cracking reaction typically deposits coke on the catalyst. Catalyst exiting the reaction zone is commonly referred to as being "spent", i.e., partially deactivated by the deposition of coke upon the catalyst. Coke is comprised of hydrogen and carbon and can include, in trace quantities, other materials such as sulfur and metals such that may enter the process with the starting material. The presence of coke interferes with the catalytic activity of the spent catalyst. It is believed that the coke blocks acid sites on the catalyst surface where the cracking reactions take place. Spent catalyst is traditionally transferred to a stripper that removes adsorbed hydrocarbons and gases from catalyst and then to a regenerator for the purpose of removing the coke by oxidation with an oxygen-containing gas. An inventory of catalyst having a reduced coke content, relative to the spent catalyst in the stripper, hereinafter referred to as regenerated catalyst, is collected for return to the reaction zone. Oxidizing the coke from the catalyst surface releases a large amount of heat, a portion of which escapes the regenerator with gaseous products of coke oxidation generally referred to as flue gas. The balance of the heat leaves the regenerator with the regenerated catalyst. The fluidized catalyst is continuously circulated between the reaction zone and the regeneration zone. The fluidized catalyst, as well as providing a catalytic function, serves as a vehicle for the transfer of heat from zone to zone. FCC processing is more fully described in U.S. Pat. No. 5,360,533 to Tagamolila et al., U.S. Pat. No. 5,584,985 to Lomas, U.S. Pat. No. 5,858,206 to Castillo and U.S. Pat. No. 6,843,906 B1 to Eng, the contents of each of these patents are hereby incorporated herein by reference. Specific details of the various contact zones, regeneration zones, and stripping zones along with arrangements for conveying the catalyst between the various zones are well known to those skilled in the art.

The FCC reactor serves to crack gas oil or heavier feeds into a broad range of products. Cracked vapors from an FCC unit enter a separation zone, typically in the form of a main column, that provides a gas stream, a gasoline cut, light cycle oil (LCO) and clarified oil (CO) which includes heavy cycle oil (HCO) components. The gas stream may include dry gas, i.e., hydrogen and $C_1$ and $C_2$ hydrocarbons, and liquefied petroleum gas ("LPG"), i.e., $C_3$ and $C_4$ hydrocarbons, also sometimes commonly referred to as wet gas.

As a result or through such hydrocarbon cracking processing, byproduct species such as $CO_2$, $H_2S$ and other sulfur compounds may form or otherwise be present in the FCC effluent in undesirably high relative amounts. In the past, amine units have been used to separate species such as $CO_2$ from hydrocarbon stream materials. In typical amine systems, an amine solvent such as methyl diethanol amine [MDEA] is used to absorb or otherwise separate $CO_2$ from hydrocarbon stream materials. A stripper is typically subsequently used to strip the absorbed $CO_2$ from the amine solvent, permitting the reuse of the stripped amine solvent.

In view of an increasing need and demand for light olefins such as ethylene and propylene for various petrochemical uses such as for the production of polyethylene, polypropylene and the like as well as the desire to produce relatively less of heavier olefins such as butylenes and pentenes which are generally less desirable as gasoline blending components due to environmental considerations, it may be desired to practice the cracking reaction processing of heavy hydrocarbon feedstock to increase the relative amount of light olefins in the resulting product slate.

Research efforts have led to the development of an FCC process that produces or results in greater relative yields of light olefins, i.e., ethylene and propylene. Such processing is more fully described in U.S. Pat. No. 6,538,169 B1 to Pittman et al., the contents of which are hereby fully incorporated herein by reference. As disclosed therein, a hydrocarbon feed stream can desirably be contacted with a blended catalyst comprising regenerated catalyst and coked catalyst. The catalyst has a composition including a first component and a second component. The second component comprises a zeolite with no greater than medium pore size wherein the zeolite comprises at least 1 wt. % of the catalyst composition. The contacting occurs in a riser to crack hydrocarbons in the feed stream and obtain a cracked stream containing hydrocarbon products including light olefins and coked catalyst. The cracked stream is passed out of an end of the riser such that the hydrocarbon feed stream is in contact with the blended catalyst in the riser for less than or equal to 2 seconds on average.

As with conventional FCC processing, byproduct species such as $CO_2$, $H_2S$ and other sulfur compounds may form or otherwise be present in the resulting effluent in undesirably high relative amounts. However, whereas conventional FCC processing effluent streams typically have little if any olefin content, the such modified hydrocarbon processing desirably produces or results in an effluent stream having a significantly large olefin content. With standard amine system treatment of such large olefin content effluent streams, some of the olefin material is typically co-absorbed with the $CO_2$ in or by the amine solvent. Such co-absorption of olefin material undesirably reduces the amounts of light olefins available for recovery from such processing.

Moreover, in conventional amine treatment processing, the amine solvent containing the absorbed $CO_2$ is typically subjected to further processing such as through a stripper wherein the absorbed $CO_2$ can desirably be separated from the amine solvent and the amine solvent can be recycled and reused for amine treatment of a selected carbon dioxide-containing stream. Unfortunately, during such subsequent stripper processing of the amine solvent, the presence of such olefin materials can lead to polymerization. Such polymerization can lead to degradation of the amine solvent and require expensive off-site reclamation processing.

Thus, there is a need and a demand for processing and arrangements for increased effectiveness for the separation and removal of carbon dioxide from high olefin content process streams.

More particularly, there is a need and a demand for improved amine treatment processing arrangements and processing schemes of such high olefin content process streams such as for the effective separation and removal of carbon dioxide therefrom while desirably permitting increased or improved olefin recovery.

SUMMARY OF THE INVENTION

A general object of at least one aspect of the invention is to provide an improved process and system for treating high olefin content carbon dioxide-containing streams.

A general object of another aspect of the invention is to provide an improved process and system for catalytic cracking a heavy hydrocarbon feedstock and obtaining light olefins substantially free of carbon dioxide.

A more specific objective of the invention is to overcome one or more of the problems described above.

The general object of a first aspect of the invention can be attained, at least in part, through a process for treating an ethylene-rich hydrocarbon and carbon dioxide-containing stream. In accordance with one preferred embodiment, such a process involves contacting at least a portion of the ethylene-rich hydrocarbon and carbon dioxide-containing stream in an absorption zone with an amine absorption solvent and at contact conditions effective to absorb a significant portion of the carbon dioxide from the contacted portion of the ethylene-rich hydrocarbon and carbon dioxide-containing stream and to form a hydrocarbon-containing process stream substantially free of carbon dioxide and a carbon dioxide-rich amine absorption solvent-containing process stream. At least a portion of the carbon dioxide-rich amine absorption solvent-containing process stream is processed in a first stripping zone at first stripping conditions effective to strip at least a portion of hydrocarbons remaining in the carbon dioxide-rich amine absorption solvent-containing process stream to form a first process stream comprising stripped hydrocarbons and a second process stream comprising carbon dioxide and amine absorption solvent. At least a portion of the second process stream is subsequently processed in a second stripping zone at second stripping conditions effective to strip at least a portion of the carbon dioxide from the second process stream to form a carbon dioxide purge stream and an amine stream.

The prior art generally fails to provide processing of high olefin content (e.g., ethylene-rich) carbon dioxide-containing streams that is as effective and efficient as generally desired. In particular, the prior art generally fails to provide effective and efficient amine system processing of high olefin content (e.g., ethylene-rich) carbon dioxide-containing streams such as for the effective separation and removal of carbon dioxide therefrom while desirably permitting increased or improved olefin recovery.

A process for treating an ethylene-rich hydrocarbon and carbon dioxide-containing stream, in accordance with another embodiment involves introducing an ethylene-rich hydrocarbon and carbon dioxide-containing stream comprising at least 20 percent ethylene into an absorption zone. At least a portion of this stream is contacted with an amine absorption solvent at contact conditions effective to absorb a significant portion of the carbon dioxide from the contacted portion of the stream. At least a portion of the contacted stream is washed to remove amine absorption solvent therefrom and to form a hydrocarbon-containing process stream substantially free of carbon dioxide and a carbon dioxide-rich amine absorption solvent-containing process stream. At least a portion of the carbon dioxide-rich amine absorption solvent-containing process stream is processed in a first stripping zone at first stripping conditions effective to strip at least a portion of hydrocarbons remaining in the carbon dioxide-rich amine absorption solvent-containing process stream to form a first process stream comprising stripped hydrocarbons and a second process stream comprising carbon dioxide and amine absorption solvent. At least a portion of the second process stream is processed in a second stripping zone at second stripping conditions effective to strip at least a portion of the carbon dioxide from the second process stream. At least a portion of the processed second process stream is washed to remove amine absorption solvent therefrom and to form a carbon dioxide purge stream and an amine stream. At least a portion of the amine stream can then desirably be recycled to the absorption zone for contact with at least a portion of the ethylene-rich hydrocarbon and carbon dioxide-containing stream.

A system for treating an ethylene-rich hydrocarbon and carbon dioxide-containing stream is also provided. In accordance with one preferred embodiment, such as system includes an absorption zone wherein at least a portion of the ethylene-rich hydrocarbon and carbon dioxide-containing stream contacts an amine absorption solvent at contact conditions effective to absorb a significant portion of the carbon dioxide from the contacted portion of the ethylene-rich hydrocarbon and carbon dioxide-containing stream to form a hydrocarbon-containing process stream substantially free of carbon dioxide and a carbon dioxide-rich amine absorption solvent-containing process stream. A first stripping zone is provided wherein at least a portion of hydrocarbons remaining in the carbon dioxide-rich amine absorption solvent-containing process stream are stripped therefrom to form a first process stream comprising stripped hydrocarbons and a second process stream comprising carbon dioxide and amine absorption solvent. The system further includes a second stripping zone wherein at least a portion of the carbon dioxide is stripped from at least a portion of the second process stream to form a carbon dioxide purge stream and an amine stream.

In accordance with another aspect of the invention there is provided a process for catalytic cracking a heavy hydrocarbon feedstock and obtaining light olefins substantially free of carbon dioxide. In accordance with one embodiment, such a process involves contacting a heavy hydrocarbon feedstock with a hydrocarbon cracking catalyst in a fluidized reactor zone to produce a hydrocarbon effluent comprising a range of hydrocarbon products, including light olefins, and a quantity of carbon dioxide. The hydrocarbon effluent is subsequently separated in a hydrocarbon separation system to form a separator liquid stream and a separator vapor stream. The separator liquid stream comprises $C_3+$ hydrocarbons substantially free of carbon dioxide. The separator vapor stream comprises $C_3-$ hydrocarbons and at least a portion of the quantity of carbon dioxide. The separator vapor stream is treated in an absorption zone to form an absorption zone effluent stream comprising $C_2-$ hydrocarbons and at least a portion of the quantity of carbon dioxide. The absorption zone effluent stream is subsequently treated in an amine treatment section with an amine absorption solvent at treatment conditions effective to absorb a significant portion of the carbon dioxide from the contacted portion of the absorption zone effluent stream and to form a hydrocarbon-containing, ethylene-rich process stream substantially free of carbon dioxide.

The prior art generally fails to provide processing schemes and arrangements for obtaining light olefins substantially free of carbon dioxide via the catalytic cracking of a heavy hydrocarbon feedstock. More particularly, the prior art generally fails to provide such processing schemes and arrangements that advantageously utilize absorption separation of hydrocarbon effluent products to produce or otherwise form process streams containing specifically desired ranges of hydrocarbons.

A process for catalytic cracking a heavy hydrocarbon feedstock and obtaining light olefins substantially free of carbon dioxide, in accordance with another embodiment involves contacting a heavy hydrocarbon feedstock with a blended catalyst comprising regenerated catalyst and coked catalyst in a fluidized reactor zone at hydrocarbon cracking reaction conditions to produce a cracked stream containing hydrocarbon products including light olefins and a quantity of carbon dioxide, said catalyst having a catalyst composition including a first component comprising a large pore molecular sieve and a second component comprising a zeolite with no greater than medium pore size, said zeolite with no greater than medium pore size comprising at least 1.0 wt. % of the catalyst composition. The hydrocarbon products are subsequently separated in a hydrocarbon separation section to form a high pressure separator liquid stream and a high pressure separator vapor stream. The high pressure separator liquid stream comprises $C_3+$ hydrocarbons substantially free of carbon dioxide. The high pressure separator vapor stream comprises $C_3-$ hydrocarbons and at least a portion of the quantity of carbon dioxide. The high pressure separator vapor stream is introduced into an absorption zone to form an absorption zone effluent stream comprising $C_2-$ hydrocarbons and at least a portion of the quantity of carbon dioxide. The absorption zone effluent stream is subsequently treated in an amine treatment section with an amine absorption solvent at treatment conditions effective to absorb a significant portion of the carbon dioxide from the contacted portion of the absorption zone effluent stream and to form a hydrocarbon-containing, ethylene-rich process stream substantially free of carbon dioxide.

A system for catalytically cracking a heavy hydrocarbon feedstock to obtain light olefins is also provided. In accordance with one preferred embodiment, such a system includes a fluidized reactor zone wherein the heavy hydrocarbon feedstock contacts a blended catalyst comprising regenerated catalyst and coked catalyst at hydrocarbon cracking reaction conditions to produce a cracked stream containing hydrocarbon products including light olefins and a quantity of carbon dioxide. A separator is provided to separate the cracked stream to form a high pressure separator liquid stream comprising $C_3+$ hydrocarbons and a high pressure separator vapor stream comprising $C_3-$ hydrocarbons and at least a portion of the quantity of carbon dioxide. An absorption zone is provided to absorb $C_3+$ hydrocarbons from the high pressure separator vapor stream to form an absorption zone effluent stream comprising $C_2-$ hydrocarbons, including ethylene, and at least a portion of the quantity of carbon dioxide. The system further includes an amine treatment section to treat the absorption zone effluent stream by contacting at least a portion of the absorption zone effluent stream with an amine absorption solvent at contact conditions effective to absorb a significant portion of the carbon dioxide from the contacted portion of the absorption zone effluent stream and to form a hydrocarbon-containing, ethylene-rich process stream substantially free of carbon dioxide and a carbon dioxide-rich amine absorption solvent-containing process stream.

As used herein, references to "light olefins" are to be understood to generally refer to $C_2$ and $C_3$ olefins, i.e., ethylene and propylene, alone or in combination. References to a process stream as "ethylene-rich" are to be understood to generally refer to such process streams as generally contain at least 20 percent ethylene and, in accordance with at least certain preferred embodiments alternatively contain at least 25 percent ethylene, at least 30 percent ethylene, at least 35 percent ethylene, at least 40 percent ethylene or about 40 to about 60 percent ethylene.

References to light olefin materials or appropriate process streams as being "substantially free of carbon dioxide" are to be understood to generally refer to such light olefin materials or process streams as desirably generally containing less than about 100 ppm of carbon dioxide, preferably containing less than about 10 ppm of carbon dioxide and, more preferably, desirably containing less than about 1 ppm of carbon dioxide. References to "$C_x$ hydrocarbon" are to be understood to refer to hydrocarbon molecules having the number of carbon atoms represented by the subscript "x". Similarly, the term "$C_x$-containing stream" refers to a stream that contains $C_x$ hydrocarbon. The term "$C_x+$ hydrocarbons" refers to hydrocarbon molecules having the number of carbon atoms represented by the subscript "x" or greater. For example, "$C_4+$ hydrocarbons" include $C_4$, $C_5$ and higher carbon number hydrocarbons. The term "$C_x-$ hydrocarbons" refers to hydrocarbon molecules having the number of carbon atoms represented by the subscript "x" or fewer. For example, "$C_4-$ hydrocarbons" include $C_4$, $C_3$ and lower carbon number hydrocarbons.

Other objects and advantages will be apparent to those skilled in the art from the following detailed description taken in conjunction with the appended claims and drawings.

Those skilled in the art and guided by the teachings herein provided will recognize and appreciate that the illustrated system or process flow diagrams have been simplified by the elimination of various usual or customary pieces of process equipment including some heat exchangers, process control systems, pumps, fractionation systems, and the like. It may also be discerned that the process flow depicted in the figures may be modified in many aspects without departing from the basic overall concept of the invention.

DETAILED DESCRIPTION

A stream rich in ethylene and containing carbon dioxide can be processed to effectively and efficiently to remove carbon dioxide therefrom. Additionally, a heavy hydrocarbon feedstock can be effectively and efficiently processed via hydrocarbon cracking processing to obtain light olefins substantially free of carbon dioxide.

Figure 1:
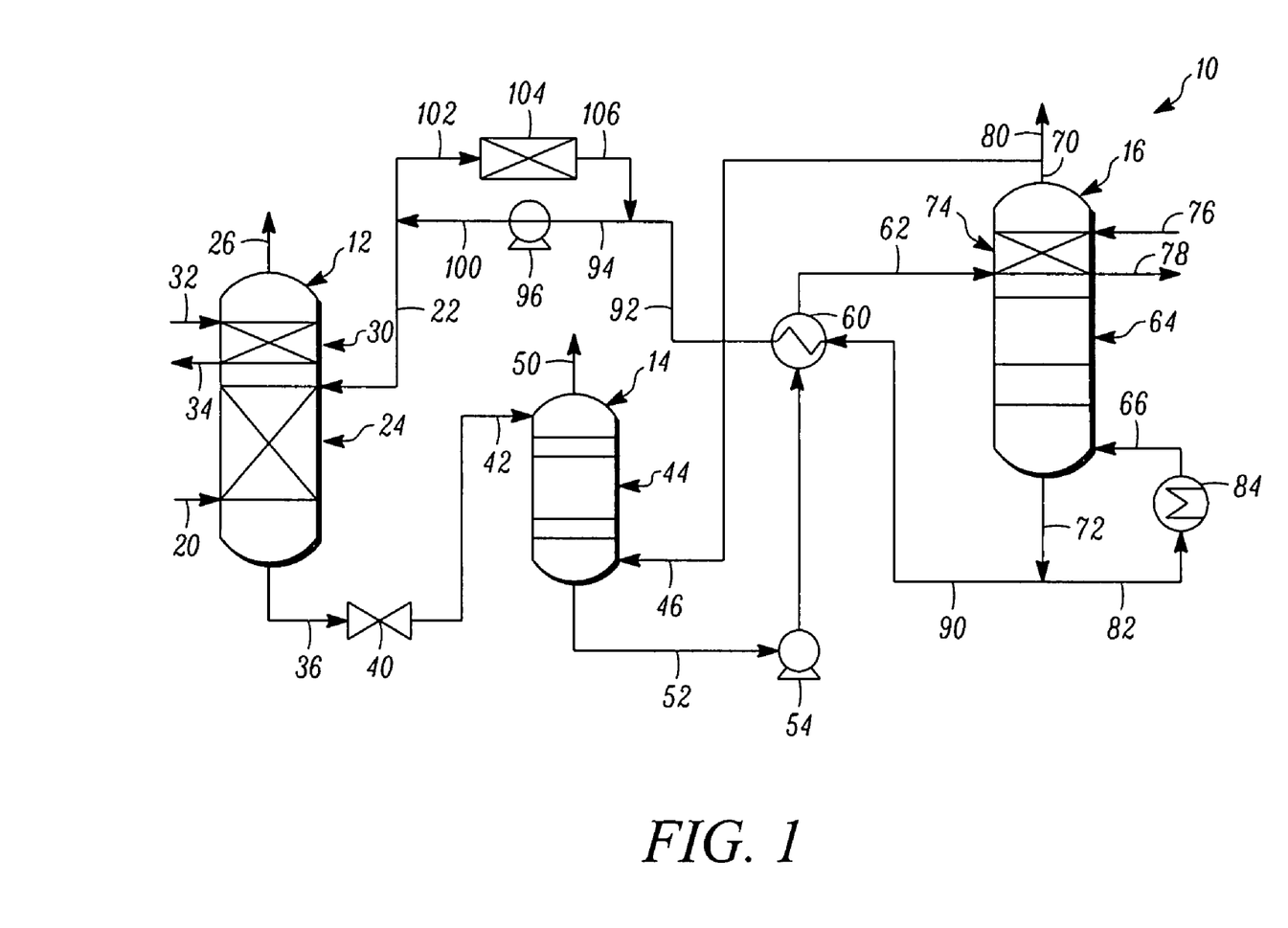
FIG. 1 is a simplified schematic diagram of an amine treatment section for the processing of a hydrocarbon process stream in accordance with one preferred embodiment.

FIG. 1 schematically illustrates an amine treatment section, generally designated by the reference numeral 10, for the processing of a hydrocarbon process stream for the removal of carbon dioxide therefrom, in accordance with one preferred embodiment. As described in greater detail below, the amine treatment section 10 includes the following major components or elements: an absorption zone 12, a first stripping zone 14 and a second stripping zone 16.

More particularly, a suitable ethylene-rich hydrocarbon and carbon dioxide-containing stream such as derived from hydrocarbon cracking processing of a heavy hydrocarbon feedstock, as described in greater detail below, is suitably introduced via a line 20 into the absorption zone 12.

As described above, ethylene-rich hydrocarbon and carbon dioxide-containing streams as used herein generally refer to carbon dioxide-containing hydrocarbon streams that typically contain somewhere in the range of about 0.5 mol. % to about 2.5 mol % carbon dioxide and also generally contain at least 20 percent ethylene and, in accordance with at least certain preferred embodiments alternatively contain at least 25 percent ethylene, at least 30 percent ethylene, at least 35 percent ethylene, at least 40 percent ethylene or about 40 to about 60 percent ethylene. In general, such a stream of material to be treated will typically be at a temperature of about 100-120° F. (38-49° C.) and a pressure in the range of about 2750-3450 kpag (about 400-500 psig).

An absorption solvent to affect desired $CO_2$ absorption is introduced into the absorption zone 12 via a line 22. Suitable absorption solvents for use in the practice of the invention include various such materials such as known in the art to effect removal of $CO_2$ and $H_2S$. Those skilled in the art and guided by the teachings herein provided will appreciate, for example, that aqueous solutions of various amine absorption solvents such as known in the art to effect removal of $CO_2$ and $H_2S$ can be used in the practice of the invention and thus the broader practice of the invention is not necessarily limited by or to practice with particular or specific absorption solvents. Suitable absorption solvents for use in the practice of the invention include tertiary amines such as methyl diethanol amine (MDEA), secondary amines such as diethanol amine (DEA) and diisopropanol amine (DIPA) and primary amines such as monoethanol amine (MEA), for example.

As will be appreciated by those skilled in the art and guided by the teachings herein provided, suitable absorption zones for use in the practice of the invention may desirably be in the form of a column and contains or includes an active absorber section or portion 24 such as includes trays, packing or other column internals such as may be desired to facilitate or otherwise help effect the desired absorption action. A suitable such amine system absorber, in accordance with one preferred embodiment, desirably operates at a pressure in the range of about 1720 kPag to about 3450 kPag (about 250 psig to about 500 psig), more preferably in a range of about 3100 kPag to about 3450 kPag (about 450 psig to about 500 psig), and with a bottoms temperature in the range of about 40° to about 80° C.

As shown, the point of introduction into the absorption zone 12 of the line 20 containing the stream of material to be treated, i.e., the ethylene-rich hydrocarbon and carbon dioxide-containing stream, may desirably be situated below the active absorber section 24 and the point of introduction into the absorption zone 12 of the line 22 containing the stream of the absorption solvent may desirably be situated above the active absorber section 24, such that the absorption solvent and the material to be treated within the absorption zone are in at least a general countercurrent flow arrangement. Moreover, such placement of the points of introduction of the stream of material to be treated and the absorption solvent, respectively, can desirably maximize the effect of any column internals and the effective contact time and residence time of the stream materials within the active absorber section 24.

A stream of treated gas is withdrawn from the absorption zone 20 via an overhead line 26. Prior to exiting the absorption zone 20, the gas is passed through a wash zone 30 where a wash material such as water is introduced through a line 32 to contact the treated gas and to desirably remove entrained absorption solvent that may have remained therewith. The used wash material containing such removed absorbent material is withdrawn from the absorption zone via a line 34 and can desirably be sent for absorption solvent recovery processing (not shown), as is known in the art.

It is to be understood that the treated gas in the overhead line 26 or one or more selected portions thereof may, if desired, be subjected to additional processing (not shown) such as via a caustic treatment step to ensure that the $CO_2$ and $H_2S$ have been suitably removed to the level required for desired light olefin product specifications.

A carbon dioxide-rich absorption solvent-containing process stream is withdrawn from the absorption zone 12 via a line 36. The carbon dioxide-rich absorption solvent-containing process stream or at least a portion thereof is passed via a valve 40 and a line 42 to the first stripping zone 14.

As will be appreciated by those skilled in the art and guided by the teachings herein provided, suitable first stripping zones for use in the practice of the invention may desirably be in the form of a column and contains or includes an active stripping section or portion 44 such as includes a selected number of trays or other stripping column internals such as may be desired to facilitate or otherwise help effect the desired stripping action. As shown, the point of introduction into the first stripping zone 14 of the line 42 containing the stream of carbon dioxide-rich absorption solvent may desirably be situated above the active stripping section 44 and the point of introduction into the first stripping zone 14 of a line 46 containing a stream of a selected stripping fluid may desirably be situated below the active stripping section 44, such that the stripping fluid and the material to be treated within the first stripping zone 14 are in at least a general countercurrent flow arrangement. Moreover, such placement of the points of introduction of the stream of material to be treated and the stripping fluid, respectively, can desirably maximize the effect of any column internals and the effective contact time and residence time of the stream materials within the first stripping zone active stripping section 44.

Thus, whereas conventional amine treatment systems such as used in the treatment of conventional FCC effluent streams may simply employ a flash column, the incorporation and use of a stripping zone such as the above-described first stripping zone 14 helps ensure the desired separation of present hydrocarbons including ethylene and propylene such as may otherwise be more strongly physisorbed than non-olefinic hydrocarbons.

In accordance with one preferred embodiment, the first stripping zone 14 desirably includes a stripper column such as having typically less than 15 ideal stages and generally no more than about 8-12 ideal stages.

The first stripping zone 14 is desirably operated in a manner, including first stripping conditions, effective to strip at least a portion of hydrocarbons remaining in the carbon dioxide-rich absorption solvent-containing process stream therefrom and to form a first process stream containing stripped hydrocarbons and a second process stream containing carbon dioxide and absorption solvent. Suitable such stripping conditions generally include: an operating pressure such as in the range of about 34 kpag to about 173 kPag (about 5 psig to about 25 psig) or, in accordance with one preferred embodiment in the range of about 34 kPag to about 69 kpag (about 5 psig to about 10 psig). Moreover, the feed rate to this stripper is desirably set so that the combined amount of ethylene and propylene in the stripper bottoms is less than 100 ppm and, in accordance with a preferred embodiment the feed rate to this stripper is desirably set so that the combined amount of ethylene and propylene in the stripper bottoms is less than 5 ppm.

A stream containing stripped hydrocarbons, including stripped ethylene and stripped propylene, is withdrawn from the first stripping zone 14 via an overhead line 50. As will be appreciated by those skilled in the art, the stream withdrawn in such overhead line may in addition to stripped hydrocarbons including ethylene and propylene also contain some minor amount, e.g., typically less than 1 wt. % of carbon dioxide.

The line 50 and the stream of stripped hydrocarbons and $CO_2$ contained therewithin can be sent for further processing such as is known in the art. For example, in accordance with one preferred embodiment, such stream or at least selected portions thereof can desirably be returned to the main column receiver so as to permit desired olefin recovery therefrom. Those skilled in the art and guided by the teachings herein provided will appreciate that while such return and processing may lead to the recycle of some $CO_2$, the amount of such recycle in practice will generally not be so significant as to make such processing uneconomical.

A process stream primarily containing absorption solvent and remaining carbon dioxide is withdrawn from the first stripping zone 14 via a line 52. The process stream in the line 52 is passed through a pump 54, a line 56, a lean/rich $CO_2$ stream heat exchanger 60 and a line 62 into the second stripping zone 16.

As will be appreciated by those skilled in the art and guided by the teachings herein provided, suitable second stripping zones for use in the practice of the invention may desirably be in the form of a column and contains or includes an active stripping section or portion 64 such as includes a selected number of trays or other stripping column internals such as may be desired to facilitate or otherwise help effect the desired stripping action. As shown, the point of introduction into the second stripping zone 16 of the line 62 containing absorption solvent and remaining carbon dioxide may desirably be situated above the active stripping section 64 and the point of introduction into the second stripping zone 16 of a line 66 containing a stream of a selected stripping fluid may desirably be situated below the active stripping section 64, such that the stripping fluid and the material to be treated within the second stripping zone 16 are in at least a general countercurrent flow arrangement. Moreover, such placement of the points of introduction of the stream of material to be treated and the stripping fluid, respectively, can desirably maximize the effect of any column internals and the effective contact time and residence time of the stream materials within the second stripping zone active section 64.

The second stripping zone 16 is desirably operated in a manner, including second stripping conditions, effective to strip at least a portion of the carbon dioxide from the second process stream to form a carbon dioxide overhead stream, shown as a line 70, and an absorption solvent bottoms stream, shown as a line 72, that is substantially free of carbon dioxide.

In general it is preferred to operate at as low a pressure as possible in order to most appropriately limit the temperature of the bottoms stream. In practice, suitable such stripping conditions generally include: an operating pressure such as in the range of about 103 kpag to about 138 kPag (about 15 psig to about 20 psig).

Prior to exiting the second stripping zone 16, the carbon dioxide overhead stream materials are passed through a wash zone 74 where a wash material, such as water, is introduced through a line 76 to contact the stripped materials and to desirably remove entrained absorbent solvent that may have remained therewith. The used wash material containing such removed absorption solvent is withdrawn from the second stripping zone 16 via a line 78 and can desirably be processed in a manner as is known in the art, such as to provide additional stripping vapor.

If desired and as shown, a first portion of the $CO_2$ overhead stream 70 can be returned to the first stripping zone 14 such as via the line 46 for use as a stripping fluid therein. A second or remaining portion of the $CO_2$ overhead stream 70 can form a purge stream, shown as in a line 80.

A first portion of the absorption solvent bottoms stream from the line 72 can pass through a line 82 to a reboiler 84 and through the line 66 back into the second stripping zone 16. A second portion of the absorption solvent bottoms stream from the line 72 can pass through a line 90 to the lean/rich $CO_2$ stream heat exchanger 60 and then through lines 92 and 94 to a recirculation pump 96 and then through lines 100 and 22 to be appropriately introduced into the absorption zone 12. A portion of the absorption solvent material in the line 100 can be processed via a line 102 through a filter device 104 and then back through a line 106 to form a portion of the stream of material in the line 94 introduced into the recirculation pump 96.

As will be appreciated by those skilled in the art and guided by the teachings herein provided, conventional amine system treatment processing may generally involve a tradeoff involving operating pressure. At low pressure operation, there is generally reduced or minimal coabsorption of hydrocarbon, but the required rate for solvent recycle is relatively large. In contrast, at high pressure operation, the solvent flow rate may desirably be reduced, but more hydrocarbons (in the case of the processing of the subject ethylene-rich streams, particularly ethylene and propylene) may be coabsorbed. With a subject amine treatment section such as described above, however, such coabsorbed ethylene and propylene is desirably recovered via the first stripping zone 14 such that the overall loss of light olefins due to amine treatment is minimized or avoided. Consequently, the subject amine treatment section can desirably be operated at relative higher pressures such as to reduce or minimize solvent recirculation. Thus, in accordance with a preferred embodiment, the absorption zone 12 and the amine absorber thereof are advantageously located at a high, if not highest, pressure location in the process scheme in order to minimize solvent recirculation.

The first stripping zone will generally operate most efficiently and require the least amount of $CO_2$ recirculation when operated at relatively low pressures. In the above-described embodiment, such as when the stream of hydrocarbons in the first stripper overhead line 50 is returned to the main column receiver, such as operates at about 34 kpag (5 psig), the pressure in the first stripping zone 14 generally needs to be high enough to permit the return of such off-gas stream to the main column receiver while allowing for line pressure drops, e.g., slightly greater than the main column receiver operating pressure.

The second stripping zone will generally operate at a pressure high enough to permit $CO_2$ to be desirably circulated to the lower portion of the first stripping zone stripper while allowing for line and unit pressure drops. This obviates the need to use a recycle blower in order to return $CO_2$ to the first stripping zone. Consequently, in a preferred embodiment, the second stripping zone preferably operates at a pressure greater than the operating pressure of the first stripping zone.

Thus, effective and efficient amine system processing of high olefin content (e.g., ethylene-rich) carbon dioxide-containing streams such as for the effective separation and removal of carbon dioxide therefrom while desirably permitting increased or improved olefin recovery are provided.

The treatment of ethylene-rich hydrocarbon and carbon dioxide-containing streams in the manner described above can find particular application in the production of light olefins via the catalytic cracking of a heavy hydrocarbon feedstock.

Figure 2:
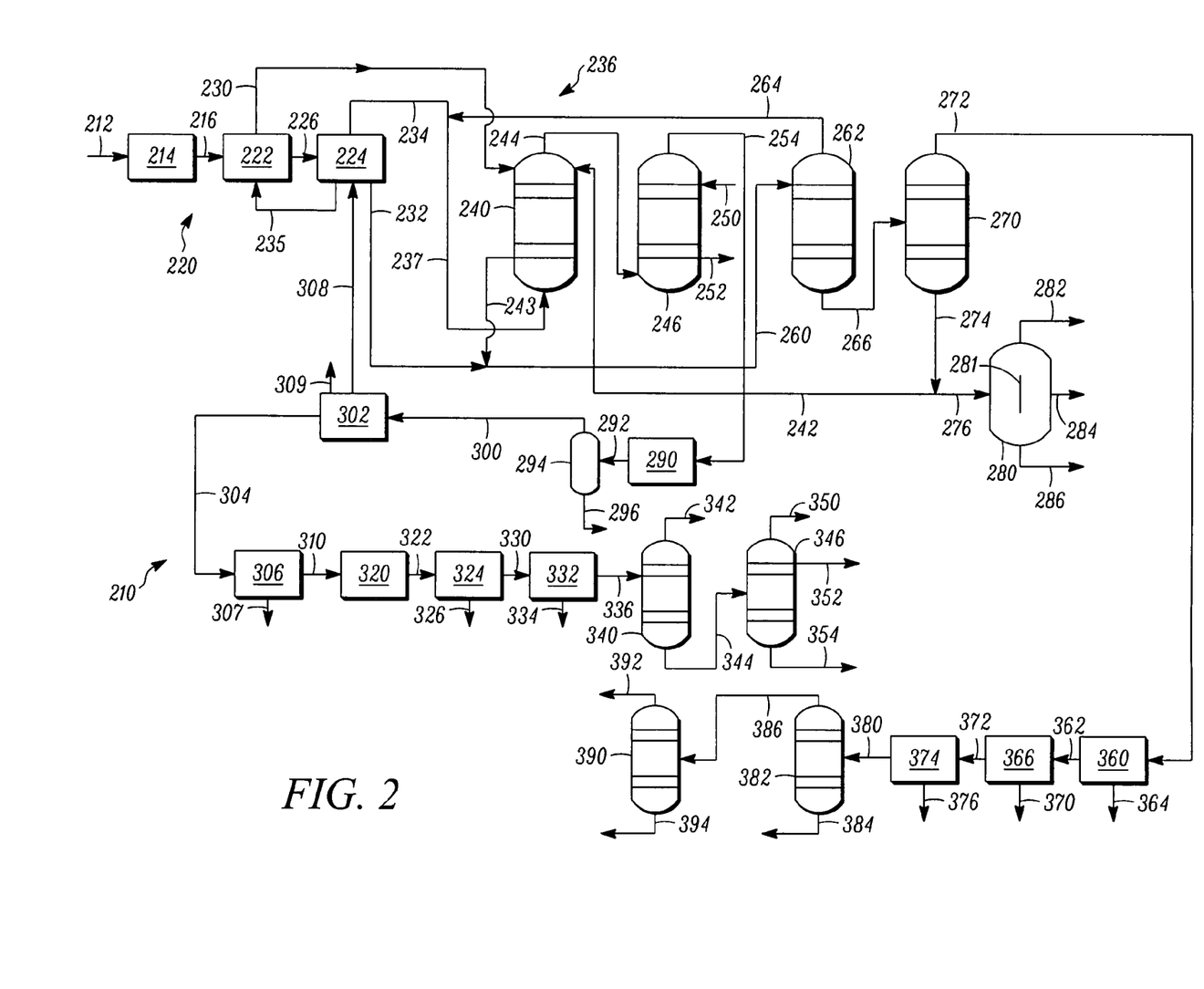
FIG. 2 is a simplified schematic diagram of a system for catalytic cracking a heavy hydrocarbon feedstock and obtaining light olefins substantially free of carbon dioxide.

Turning to FIG. 2, there is illustrated a simplified schematic diagram of a system, generally designated by the reference numeral 210, for catalytic cracking a heavy hydrocarbon feedstock and obtaining light olefins substantially free of carbon dioxide, in accordance with one embodiment of the invention.

In the system 210, a suitable heavy hydrocarbon feedstock stream is introduced via a line 212 into a fluidized reactor zone 214 wherein the heavy hydrocarbon feedstock contacts with a hydrocarbon cracking catalyst zone to produce a hydrocarbon effluent comprising a range of hydrocarbon products, including light olefins, and a quantity of carbon dioxide.

Suitable fluidized catalytic cracking reactor zones for use in the practice of such an embodiment may, as is described in above-identified U.S. Pat. No. 6,538,169 B1 to Pittman et al., include a separator vessel, a regenerator, a blending vessel, and a vertical riser that provides a pneumatic conveyance zone in which conversion takes place. The arrangement circulates catalyst and contacts feed in a specifically described manner.

More specifically and as described therein, the catalyst typically comprises two components that may or may not be on the same matrix. The two components are circulated throughout the entire system. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as a Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. It has been found that Y zeolites with low rare earth content are preferred in the first catalyst component. Low rare earth content denotes less than or equal to about 1.0 wt-% rare earth oxide on the zeolite portion of the catalyst. Octacat™ catalyst made by W. R. Grace & Co. is a suitable low rare earth Y-zeolite catalyst.

The second catalyst component comprises a catalyst containing, medium or smaller pore zeolite catalyst exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium or smaller pore zeolites include ferrierite, erionite, and ST-5, developed by Petroleos de Venezuela, S.A. The second catalyst component preferably disperses the medium or smaller pore zeolite on a matrix comprising a binder material such as silica or alumina and an inert filer material such as kaolin. The second component may also comprise some other active material such as Beta zeolite. These catalyst compositions have a crystalline zeolite content of 10-25 wt. % or more and a matrix material content of 75-90 wt. %. Catalysts containing 25 wt. % crystalline zeolite material are preferred. Catalysts with greater crystalline zeolite content may be used, provided they have satisfactory attrition resistance. Medium and smaller pore zeolites are characterized by having an effective pore opening diameter of less than or equal to 0.7 nm, rings of 10 or fewer members and a Pore Size Index of less than 31. The total catalyst composition should contain 1-10 wt. % of a medium to small pore zeolite with greater than or equal to 1.75 wt. % being preferred. When the second catalyst component contains 25 wt. % crystalline zeolite, the composition contains 4-40 wt. % of the second catalyst component with a preferred content of greater than or equal to 7 wt. %. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit.

The high concentration of the medium or smaller pore zeolite in the second component of the catalyst composition improves selectivity to light olefins by further cracking the lighter naphtha range molecules. But at the same time, the resulting smaller concentration of the first catalyst component still exhibits sufficient activity to maintain conversion of the heavier feed molecules to a reasonably high level.

The relatively heavier feeds suitable for processing in accordance herewith include conventional FCC feedstocks or higher boiling or residual feeds. A common conventional feedstock is vacuum gas oil which is typically a hydrocarbon material prepared by vacuum fractionation of atmospheric residue and which has a broad boiling range of from 315-622° C. (600-1150° F.) and, more typically, which has a narrower boiling point range of from 343-551° C. (650-1025° F.). Heavy or residual feeds, i.e., hydrocarbon fractions boiling above 499° C. (930° F.), are also suitable. The fluidized catalytic cracking processing the invention is typically best suited for feedstocks that are heavier than naptha range hydrocarbons boiling above about 177° C. (350° F.).

The effluent or at least a selected portion thereof is passed from the fluidized reactor zone 214 through a line 216 into a hydrocarbon separation system 220, such as includes a main column section 222 and a staged compression section 224. The main column section 222 may desirably include a main column separator with an associated main column overhead high pressure receiver wherein the fluidized reactor zone effluent can be separated into desired fractions including a main column vapor stream, such as passed through a line 226, and a main column liquid stream, such as passed through a line 230.

To facilitate illustration and discussion, other fraction lines such as including a heavy gasoline stream, a light cycle oil ("LCO") stream, a heavy cycle oil ("HCO") stream and a clarified oil ("CO") stream, for example, may not here be shown nor hereinafter specifically described.

The main column vapor stream line 226 is introduced into the staged compression section 224, such as constituting a two-stage compression. The staged compression section 224 results in the formation of a high pressure separator liquid stream in a line 232 and a high pressure separator vapor stream in a line 234. While the pressure of such high pressure liquid and high pressure vapor can vary, in practice such streams are typically at a pressure in the range of about 1375 kPag to about 2100 kPag (about 200 psig to about 300 psig). The compression section 224 may also result in the formation of a stream of spill back materials largely composed of heavier hydrocarbon materials and such as can be returned to the main column section 222 via a line 235.

The high pressure separator liquid stream includes $C_3+$ hydrocarbons and is substantially free of carbon dioxide. The high pressure separator vapor stream includes $C_3$-hydrocarbons and includes a quantity of carbon dioxide.

The separator vapor stream line 234 is introduced into an absorption zone, generally designated by the reference numeral 236, via a line 237. The absorption zone 236 includes a primary absorber 240 wherein the separator vapor stream contacts with a debutanized gasoline material provided by the line 242 and the main column liquid stream provided by the line 230 to absorb $C_3+$ and separate $C_2$ and lower boiling fractions from the gas to the primary absorber 240. In general, the absorption zone 236 includes a primary absorber that suitably includes a plurality of stages with at least one and preferably two or more intercoolers interspaced therebetween to assist in achieving desired absorption. In practice, such a primary absorber typically includes about five absorber stages between each pair intercoolers. Thus, a primary absorber to achieve desired absorption in accordance with one preferred embodiment desirably includes at least about 15 ideal stages with at least 2 intercoolers appropriately spaced therebetween. In another preferred embodiment, a suitable preferred primary absorber to achieve desired absorption desirably includes at least about 20 ideal stages with at least 3 intercoolers appropriately spaced therebetween. In yet another preferred embodiment, a suitable preferred primary absorber to achieve desired absorption desirably includes at about 20 to about 25 ideal stages with 4 or more intercoolers appropriately spaced therebetween. While the broader practice of the invention is not necessarily so limited, in at least certain preferred embodiments, it has been found advantageous to employ propylene as a refrigerant in one or more of such primary absorber the intercoolers to assist in achieving the desired absorption.

$C_3+$ hydrocarbons absorbed in or by the debutanized gasoline and main column liquid can be passed via a line 243 for further processing in accordance with the invention as later described herein.

The off gas from the primary absorber 240 passes via a line 244 to a secondary or sponge absorber 246. The secondary absorber 246 contacts the off gas with light cycle oil from a line 250. Light cycle oil absorbs most of the remaining $C_4$ and higher hydrocarbons and returns to the main fractionators via a line 252. A stream of $C_2-$ hydrocarbons is withdrawn as off gas from the secondary or sponge absorber 246 in a line 254 for further treatment as later described herein.

The separator liquid stream in the line 232 and contents from the line 243 are passed through a line 260 into a stripper 262 which removes most of the $C_2$ and lighter gases in a line 264. In practice, such a stripper can desirably be operated at a pressure in the range of about 1650 kPag to about 1800 kPag (about 240 psig to about 260 psig) with a $C_2/C_3$ molar ratio in the stripper bottoms of less than 0.001 and preferably with a $C_2/C_3$ molar ratio in the stripper bottoms of less than about 0.0002 to about 0.0004.

As shown, $C_2$ and lighter gases in the line 264 can desirably be combined with high pressure separator vapor from the line 234 to form the line 237 that is fed into the primary absorber 240. The stripper 262 supplies a liquid $C_3+$ stream via a line 266 to a debutanizer 270. A suitable such debutanizer, in accordance with one preferred embodiment, includes a condenser (not specifically shown) that desirably operates at a pressure in the range of about 965 kpag to about 1105 kPag (about 140 psig to about 160 psig), with no more than about 5 mol % $C_5$ hydrocarbons in the overhead and no more than about 5 mol % $C_4$ hydrocarbons in the bottoms. More preferably, the relative amount of $C_5$ hydrocarbons in the overhead is less than about 1-3 mol % and the relative amount of $C_4$ hydrocarbons in the bottoms is less than about 1-3 mol %.

A stream of $C_3$ and $C_4$ hydrocarbons from the debutanizer 270 are taken overhead by a line 272 for further treatment, such as later described herein.

A line 274 withdraws a stream of debutanized gasoline from the debutanizer 270. A portion of the stream of debutanized gasoline is returned to the primary absorber 240 via the line 242 to serve as the first absorption solvent. Another portion of the stream of debutanized gasoline is passed in a line 276 to a naptha splitter 280.

In accordance with one preferred embodiment, the naptha splitter 280 is desirably in the form of a dividing wall separation column, such as having a dividing wall 281 positioned therewithin. Such a dividing wall separation column naptha splitter is desirably effective to separate the debutanized gasoline introduced therein into a light fraction stream comprising compounds containing five to six carbon atoms, an intermediate fraction stream comprising compounds containing seven to eight carbon atoms, and a heavy fraction stream comprising compounds containing more than eight carbon atoms. More specifically, such a dividing wall separation column may generally operate at a condenser pressure in the range of about 34 kpag to about 104 kPag (about 5 psig to about 15 psig) and, in accordance with one embodiment operated at a condenser pressure of about 55 kpag to about 85 kPag (about 8 psig to about 12 psig).

Such light, intermediate and heavy fraction streams, are appropriately passed via corresponding lines 282, 284, and 286, respectively, for further processing or product recovery, as may be desired.

Returning to the processing of the stream of $C_2-$ hydrocarbons withdrawn from the secondary or sponge absorber 246 in the line 254, such stream materials can be passed through a further compression section 290 to form a line 292 that is passed into a compression or discharge drum 294. The discharge drum 294 forms a knockout stream generally composed of heavy components (e.g., $C_3+$ hydrocarbons that liquefy in the discharge drum 294) and such as withdrawn in a line 296. The discharge drum 294 also forms an overhead stream that primarily comprising $C_2-$ hydrocarbons, with typically no more than trace amounts (e.g., less than 1 wt. %) of $C_3+$ hydrocarbons, and a quantity of carbon dioxide, withdrawn in a line 300.

The overhead stream in the line 300 is passed to an amine treatment section 302 such as described above, to effect $CO_2$ removal therefrom. A stream containing $C_2-$ hydrocarbons substantially free of carbon dioxide is passed through a line 304 to a drier section 306 with water withdrawn therefrom in a line 307. A stream containing stripped hydrocarbons and possibly minor amounts (e.g., typically less than 1 wt. %) of $CO_2$ is conveyed via a line 308 such as back to the compression section 224 such as for further processing such as consistent with the above description. A stream containing $CO_2$ rich purge gas, such as corresponding to the purge line 80 from the second stripping zone 16 in the above-described amine treatment system 10, is conveyed from the amine treatment section 302 via a line 309.

A stream containing dried $C_2-$ hydrocarbons substantially free of carbon dioxide is passed via a line 310 to an acetylene conversion section or unit 320. As is known in the art, acetylene conversion sections or units are effective to convert acetylene to form ethylene. Thus, an additionally ethylene-enriched process stream is withdrawn in a line 322 from the acetylene conversion section or unit 320.

As the acetylene conversion may result in additional formation of water, the process stream in the line 322 can, if desired, be introduced into an optional drier unit 324 such as with water being withdrawn therefrom in a line 326 and with the resulting dried process stream passed via a line 330 to an optional further treatment section 332 such as in the form of a $CO_2$, carbonyl sulfide ("COS"), Arsine and/or Phosphine treater as is known in the art to effect removal of $CO_2$, COS, Arsine and/or Phosphine, withdrawn in a line 334, and a treated stream such as withdrawn in a line 336.

The treated stream in the line 336 may desirably be introduced into a demethanizer 340. A suitable such demethanizer, in accordance with one preferred embodiment, includes a condenser (not specifically shown) that desirably operates at a temperature of no greater than about −90° C. (−130° F.), more preferably operates at a temperature in the range of about −90° C. to about −102° C., preferably about −96° C. (−130° to about −150° F., preferably at about −140° F.). In addition, a preferred demethanizer for use in the practice of the invention desirably operates with a methane to ethylene molar ratio in the bottoms of no greater than about 0.0005 and, more preferably at a methane to ethylene molar ratio in the bottoms of no greater than about 0.0003 to about 0.0002.

A stream of methane and hydrogen gas from the demethanizer 340 is taken overhead via a line 342 such as for use as a fuel or, if desired for further processing or treatment such as to a pressure swing absorption unit (not shown) for $H_2$ recovery.

A line 344 withdraws a stream of demethanized material from the demethanizer 340. The line demethanized material 344 is passed to an ethylene/ethane splitter 346. A suitable such ethylene/ethane splitter, in accordance with one preferred embodiment, includes a condenser (not specifically shown) that desirably operates at a pressure in the range of about 1930 kPag to about 2105 kpag (about 280 psig to about 305 psig), and desirably operates such that there is no more than about 0.5 vol. % ethane in the ethylene product stream, preferably less than about 0.1 vol. % ethane in the ethylene product stream and, more preferably, less than about 0.05 vol. % ethane in the ethylene product stream.

The ethylene/ethane splitter 346 forms a vapor stream of remaining light ends, a partial condensate stream of ethylene and a bottoms stream of ethane which are passed through lines 350, 352 and 354, respectively, such as either for product recovery or further desired processing, as is known in the art.

Returning to the processing of the stream containing $C_3$ and $C_4$ hydrocarbons taken overhead from the debutanizer 270 via the line 272, as such a process stream may contain some significant relative amounts of hydrogen sulfide, the line 272 can desirably be passed to a sulfide removal treatment unit 360 such as known in the art, such as in the form of an amine treatment section, such as to form a treated stream passed via a line 362. The hydrogen sulfide content of the treated stream is desirably reduced down to about 20 ppm, with hydrogen sulfide being removed via a line 364.

If desired or required, the treated stream line 362 can be introduced into an optional caustic treatment or the like section 366 such as to effect further hydrogen sulfide removal such as down to a hydrogen sulfide content of 1 ppm or less. Hydrogen sulfide is shown as removed from the caustic treatment section 366 via a line 370.

A treated stream with an appropriately reduced hydrogen sulfide content is passed via a line 372 to a mercaptan treatment section 374, such as to effect mercaptan removal from the stream materials such as via caustic wash as is known in the art. Mercaptans are shown as removed via a line 376.

The resulting stream is passed via a line 380 to $C_3/C_4$ splitter 382. A suitable such $C_3/C_4$ splitter, in accordance with one preferred embodiment, includes a condenser (not specifically shown) that desirably operates at a pressure in the range of about 1650 kpag to about 1800 kPag (about 240 psig to about 260 psig), preferably at a pressure of about 1724 kpag (about 250 psig) and desirably operates such that there is no more than about 5 mol. % $C_4$s in the overhead product stream, preferably less than about 1 mol. % $C_4$s in the overhead product stream and no more than about 5 mol. % $C_3$s in the bottoms stream, preferably less than about 1 mol. % $C_3$s in the bottoms stream.

The $C_3/C_4$ splitter 382 forms a stream of $C_4+$ hydrocarbons which is passed through a line 384 such as either for product recovery or further desired processing, as is known in the art.

The $C_3/C_4$ splitter 382 also forms a stream composed primarily of $C_3$ hydrocarbons which is passed through a line 386.

The stream in the line 386 can be passed to a propylene/propane splitter 390. A suitable such propane/propylene splitter, in accordance with one preferred embodiment, desirably operates such that at least 98 wt. % and, preferably, at least about 99 wt. % of the propylene recovery is in the overhead stream and the propylene in the overhead stream is at least about 99.5% pure.

The propylene/propane splitter 390 forms a stream of propylene and a stream of propane which are passed through lines 392 and 394, respectively, such as either for product recovery or further desired processing, as is known in the art.

Thus processing schemes and arrangements are desirably provided for obtaining light olefins substantially free of carbon dioxide via the catalytic cracking of a heavy hydrocarbon feedstock. More particularly, processing schemes and arrangements are provided that advantageously utilize absorption separation of hydrocarbon effluent products to produce or otherwise form process streams containing specifically desired ranges of hydrocarbons.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention. For example, while the invention has been described above making specific reference to an embodiment wherein the amine treatment section 302 is placed downstream of the further compression section 290, those skilled in the art and guided by the teachings herein provided will appreciate that the broader practice of the invention is not necessarily so limited. This in certain embodiments it may be desired that the amine treatment section be disposed upstream of such further compression.

What is claimed is:

1. A process for treating an ethylene-rich hydrocarbon and carbon dioxide-containing stream, said process comprising:

contacting at least a portion of the ethylene-rich hydrocarbon and carbon dioxide-containing stream in an absorption zone with an amine absorption solvent and at contact conditions effective to absorb a significant portion of the carbon dioxide from the contacted portion of the ethylene-rich hydrocarbon and carbon dioxide-containing stream and to form a hydrocarbon-containing process stream substantially free of carbon dioxide and a carbon dioxide-rich amine absorption solvent-containing process stream including ethylene;

processing at least a portion of the carbon dioxide-rich amine absorption solvent-containing process stream in a first stripping zone at first stripping conditions effective to strip at least a portion of hydrocarbons remaining in the carbon dioxide-rich amine absorption solvent-containing process stream to form a first process stream comprising stripped hydrocarbons including ethylene and less than 1 wt % of carbon dioxide and a second process stream comprising carbon dioxide and amine absorption solvent; and processing at least a portion of the second process stream in a second stripping zone at second stripping conditions effective to strip at least a portion of the carbon dioxide from the second process stream to form a carbon dioxide purge stream and an amine stream.

2. The process of claim 1 wherein the amine stream is substantially free of carbon dioxide.

3. The process of claim 1 wherein the ethylene-rich hydrocarbon and carbon dioxide-containing stream comprises at least 20 percent ethylene.

4. The process of claim 1 wherein the ethylene-rich hydrocarbon and carbon dioxide-containing stream comprises at least 25 percent ethylene.

5. The process of claim 1 wherein the ethylene-rich hydrocarbon and carbon dioxide-containing stream comprises at least 30 percent ethylene.

6. The process of claim 1 wherein the ethylene-rich hydrocarbon and carbon dioxide-containing stream comprises at least 35 percent ethylene.

7. The process of claim 1 wherein the ethylene-rich hydrocarbon and carbon dioxide-containing stream comprises at least 40 percent ethylene.

8. The process of claim 1 wherein the ethylene-rich hydrocarbon and carbon dioxide-containing stream comprises about 40 to about 60 percent ethylene.

9. The process of claim 1 wherein the first stripper conditions and the second stripper conditions each include an operating pressure and wherein the operating pressure of the first stripper is less than the operating pressure of the second stripper.

10. The process of claim 9 wherein the operating pressure of the first stripper is in the range of about 34 kPag to about 69 kPag.

11. The process of claim 10 wherein the operating pressure of the second stripper is in the range of about 103 kPag to about 138 kPag.

12. The process of claim 9 wherein the operating pressure of the second stripper is in the range of about 103 kPag to about 138 kPag.

13. The process of claim 1 wherein the first and the second strippers each comprise a stage-containing stripper and wherein the second stripper comprises more stages than the first stripper.

14. A process for treating an ethylene-rich hydrocarbon and carbon dioxide-containing stream, said process comprising:

introducing an ethylene-rich hydrocarbon and carbon dioxide-containing stream comprising at least 20 percent ethylene into an absorption zone;

contacting at least a portion of said stream in the absorption zone with an amine absorption solvent and at contact conditions effective to absorb a significant portion of the carbon dioxide from the contacted portion of said stream and washing at least a portion of the contacted stream to remove amine absorption solvent therefrom and to form a used wash material stream separately removed from the absorption zone, a hydrocarbon-containing process stream substantially free of carbon dioxide and a carbon dioxide-rich amine absorption solvent-containing process stream including ethylene;

processing at least a portion of the carbon dioxide-rich amine absorption solvent-containing process stream in a first stripping zone at first stripping conditions effective to strip at least a portion of hydrocarbons remaining in the carbon dioxide-rich amine absorption solvent-containing process stream to form a first process stream comprising stripped hydrocarbons and less than 1 wt % of carbon dioxide and a second process stream comprising carbon dioxide and amine absorption solvent;

processing at least a portion of the second process stream in a second stripping zone at second stripping conditions effective to strip at least a portion of the carbon dioxide from the second process stream and washing at least a portion of the processed second process stream to remove amine absorption solvent therefrom and to form a carbon dioxide purge stream and an amine stream; and recycling at least a portion of the amine stream to the absorption zone for contact with at least a portion of the ethylene-rich hydrocarbon and carbon dioxide-containing stream.

15. The process of claim 14 wherein the ethylene-rich hydrocarbon and carbon dioxide-containing stream comprises at least 30 percent ethylene.

16. The process of claim 14 wherein the ethylene-rich hydrocarbon and carbon dioxide-containing stream comprises about 40 to about 60 percent ethylene.

17. The process of claim 14 wherein the first stripper conditions and the second stripper conditions each include an operating pressure and wherein the operating pressure of the first stripper is less than the operating pressure of the second stripper.

18. The process of claim 14 wherein the operating pressure of the first stripper is in the range of about 34 kPag to about 69 kPag.

19. The process of claim 14 wherein the operating pressure of the second stripper is in the range of about 103 kPag to about 138 kPag.

\* \* \* \* \*